United States Patent
Chang et al.

(10) Patent No.: US 10,321,679 B2
(45) Date of Patent: Jun. 18, 2019

(54) LAMINATE FOR INHIBITING ETHYLENE RESPONSE IN PLANTS AND A METHOD FOR PREPARING THE SAME

(71) Applicants: Shanghai Lytone Biochemicals Ltd., Shanghai (CN); Lytone Enterprise, Inc., New Taipei (TW)

(72) Inventors: William T. H. Chang, New Taipei (TW); Hsiying Chen, New Taipei (TW); Yuming Chang, New Taipei (TW)

(73) Assignees: Shanghai Lytone Biochemicals, LTD., Shanghai (CN); Lytone Enterprise, Inc., New Taipei (TW)

( * ) Notice: Subject to any disclaimer, the term of this patent is extended or adjusted under 35 U.S.C. 154(b) by 0 days.

(21) Appl. No.: 15/432,020

(22) Filed: Feb. 14, 2017

(65) Prior Publication Data

US 2017/0150716 A1    Jun. 1, 2017

Related U.S. Application Data

(63) Continuation of application No. PCT/CN2014/092350, filed on Nov. 27, 2014.

(30) Foreign Application Priority Data

Aug. 14, 2014  (CN) .......................... 2014 1 0399824

(51) Int. Cl.
    *A01N 27/00*  (2006.01)
    *A01N 25/32*  (2006.01)
    *A01N 3/00*   (2006.01)

(52) U.S. Cl.
    CPC .............. *A01N 27/00* (2013.01); *A01N 3/00* (2013.01); *A01N 25/32* (2013.01)

(58) Field of Classification Search
    None
    See application file for complete search history.

(56) References Cited

U.S. PATENT DOCUMENTS

| | | | |
|---|---|---|---|
| 3,879,188 A | 4/1975 | Fritz et al. | |
| 4,633,276 A | 12/1986 | Shibata et al. | |
| 5,100,462 A | 3/1992 | Sisler et al. | |
| 5,518,988 A | 5/1996 | Sisler et al. | |
| 6,017,849 A | 1/2000 | Daly et al. | |
| 2002/0061822 A1 | 5/2002 | Kostansek | |
| 2002/0198107 A1 | 12/2002 | Kostansek | |
| 2005/0250649 A1 | 11/2005 | Jacobson et al. | |
| 2005/0260907 A1 | 11/2005 | Chang et al. | |
| 2011/0143004 A1* | 6/2011 | Wood ....................... | A01N 3/00 426/324 |
| 2012/0258220 A1 | 10/2012 | Jacobson | |

FOREIGN PATENT DOCUMENTS

| | | |
|---|---|---|
| AU | 2014227556 B2 | 9/2016 |
| CA | 2692211 * | 8/2010 |
| CN | 1346594 A | 5/2002 |
| CN | 1371603 A | 10/2002 |
| CN | 1440649 A | 9/2003 |
| CN | 1703955 A | 12/2005 |
| CN | 102726377 A | 10/2012 |
| CN | 102740692 A | 10/2012 |
| JP | 2003286101 A | 10/2003 |
| JP | 2005053332 A | 3/2005 |
| JP | 2005320328 A | 11/2005 |
| TW | I265005 B | 11/2006 |
| TW | 201427598 A | 7/2014 |
| WO | WO-0224171 A1 | 3/2002 |
| WO | WO-2008089140 A1 | 7/2008 |
| WO | WO-2011081877 | 7/2011 |
| WO | WO-2014085518 | 6/2014 |

OTHER PUBLICATIONS

International Search Report and Written Opinion and its English translation for PCT/CN2014/092350 filed Nov. 27, 2014 (published as WO2016023297 published Feb. 18, 2016) which is the parent application to the instant application, dated May 6, 2015, 22 pages.

(Continued)

*Primary Examiner* — Alton N Pryor
(74) *Attorney, Agent, or Firm* — Harness, Dickey & Pierce, P.L.C.; Anthony G. Fussner

(57) ABSTRACT

A laminate for inhibiting ethylene response in plants comprises at least one layer of a polymer composition and at least one layer of a paper substrate. The polymer composition comprises an agent that blocks binding sites for ethylene response in plants, a solvent having slight solvency or no solvency, and a polymer or copolymer soluble in the solvent and water. Also disclosed are methods of preparing the same, methods for preparing the paper substrate laminate, and methods for inhibiting ethylene response in plants. An aluminum foil-based or corrugated board-based laminate for inhibiting ethylene response in plants comprises at least one layer of a polymer composition and at least one layer of aluminum foil or corrugated board. The polymer composition comprises an agent that blocks binding sites for ethylene response in plants, a solvent having slight solvency or no solvency, and a polymer or copolymer soluble in the solvent and water.

17 Claims, No Drawings

(56) References Cited

OTHER PUBLICATIONS

Sister et al., Plant Growth Reg. 9, 157-194, 1990, Competition of cyclooctenes and cyclooctadienes for ethylene binding and activity in plants.

Chinese Office Action and its English translation dated Feb. 4, 2017 for Chinese patent application No. 201410399824.0 which is the parent application to the instant application, 8 pages.

European Search Report dated Nov. 24, 2017 for EP Application No. 14899768.7 which claims priority to the same parent application as the instant application; 13 pages.

Second Chinese Office Action and Search Report (and its English translation) dated Dec. 20, 2017 for Chinese application No. 2014103998240 which claims priority to the same parent application as the instant application; 22 pages.

Third Chinese Office Action and Search Report (and its English translation) dated Nov. 2, 2018 for Chinese application No. 2014103998240 which claims priority to the same parent application as the instant application; 38 pages.

Japanese Second Office Action and its English translation for JP2017-527957 which claims priority to the same parent application as the instant application, dated Apr. 16, 2019, 9 pages.

\* cited by examiner

LAMINATE FOR INHIBITING ETHYLENE RESPONSE IN PLANTS AND A METHOD FOR PREPARING THE SAME

CROSS-REFERENCE TO RELATED APPLICATIONS

This application is a continuation of and claims the benefit and priority of PCT International Application No. PCT/CN2014/092350 filed Nov. 21, 2014 published Feb. 18, 2016 as WO2016/023297 which claims priority to Chinese application No. 201410399824.0 filed Aug. 14, 2014. The entire disclosures of the above applications are incorporated herein by reference.

TECHNICAL FIELD

The present disclosure generally relates to a laminate for inhibiting ethylene response in plants, comprising a layer of a polymer composition having an agent that blocks binding sites for ethylene response in plants, and a method for preparing the same. In particular, the present disclosure relates to a paper substrate laminate, a method for preparing the paper substrate laminate and a method for inhibiting ethylene response in plants by using the laminate according to the present disclosure.

BACKGROUND

This section provides background information related to the present disclosure which is not necessarily prior art.

A cyclopropene-based compound, 1-methylcyclopropene (1-MCP), is a highly effective inhibitor for ethylene receptor, which functions by acting irreversibly on the ethylene receptor in a manner of binding preferentially to the ethylene receptor, blocking the binding of an endogenous ethylene and an exogenous ethylene to the ethylene receptor, thereby inhibiting a series of physiological and biochemical reactions including after-ripening or aging of horticultural plants such as flowers, vegetables and fruits, so as to attain an objective of preserving foods such as flowers, vegetables and fruits in storage and transportation.

1-MCP is a highly reactive olefin, having a boiling point of 10° C., present in gas form at normal temperature. A fumigation method is carried out in on-site operation in a manner that an amount of 1-MCP gas is predetermined and then placed into a closed space to function, which is therefore very inconvenient in use. In order to enhance the convenience for using 1-MCP and the stability during the storage thereof, U.S. Pat. No. 6,017,849 proposed a method for encapsulating 1-MCP with a carrier, for example, a carrier of α-cyclodextrin could be used for stabilizing the reactivity and instability of 1-MCP gas.

The cyclodextrin is a cyclic glucose oligosaccharide, having a special cylinder-shaped structure. The glucose monomer has a polar hydroxyl group located on the surface of the cylinder structure, rendering the external of the cyclodextrin hydrophilic. On the contrary, the cylindrical inner hole is non-polar and lipophilic, so the inner hole of the cyclodextrin can form a complex with the other molecules, which can be released under a certain condition. Recently, the cyclodextrin has been widely used in fields such as foods, pharmacy, chemical, agriculture and environmental engineering. Currently, there are crystals having 6, 7, 8 or 9 glucose units linked annularly via α-1,4 linkages, referred as α-Cyclodextrin, β-Cyclodextrin, γ-Cyclodextrin or δ-Cyclodextrin, respectively.

The technique of solid 1-MCP is mainly to use the cyclodextrin to immobilize 1-MCP gas, which can be released upon mixing the powder with water or a buffer solution, thereby the application range of 1-MCP can be extended. When use on-site, it is only necessary to add water or a buffer solution, thus the trouble of gas transportation can be avoided and the convenience for on-site staffs operation can be enhanced. Therefore, an easy and safe method for storing, transporting, using or delivering the gas to a plant can be provided. The technique for immobilizing 1-MCP gas with cyclodextrin has been successfully commercialized and marketed and approved in 1999 by EPA (Environmental Protection Agency) in US.

Although the solid powder product is much more convenient in use than the gaseous product, it still has a number of limitation and disadvantages in the application, and is disadvantageous for use by general users. Therefore, the development of various dosages of 1-MCP becomes a focus for the subsequent commercial applications of 1-MCP. PCT Patent Application Publication No. WO 02/24171A1 discloses an effervescent tablet dosage formulation which alleviates the disadvantages of mixing associated with the powder form. This product of tablet dosage is easily metered, and has a controlled release mechanism which cannot be achieved by the powder type formulation. As compared with the powder type product, these tablet dosages are easy to use for non-specialized customers, florists and wholesalers. However, these effervescent tablet dosage products of 1-MCP still have limitation in use, since it is usually necessary to circulate air to ensure a uniform distribution of 1-MCP gas. If 1-MCP has a non-uniform concentration in atmospheric environment, it tends to cause a non-uniform ripening response in plants. However, the requirement of using circulating air in a wild field is not easy to meet, which may further lead to an impairment of the commercial benefits of the product.

TW Patent No. I 265005 discloses a non-woven fabric-based laminate which is prepared by interposing a composition, including 1-MCP and a thermoplastic polymer, between non-woven fabrics or other layered materials, and immobilizing 1-MCP onto the layered materials and bonding the layered materials through the adhesion effect of the thermoplastic polymer. However, during the preparation, it is necessary to mix the 1-MCP powders with the thermoplastic polymer powders before spraying the powders directly onto the non-woven fabric, thus a problem of non-uniform distribution of 1-MCP may occur easily, which may further result in a non-uniform releasing concentration of the product 1-MCP.

SUMMARY

This section provides a general summary of the disclosure, and is not a comprehensive disclosure of its full scope or all of its features.

In order to address the current problems, such as inconvenience of use, non-uniform distribution and limitations of application, present in various dosages for inhibiting ethylene response in plants, the present disclosure provides a method for preparing a preservative paster, which can be applied in storage and transportation and expected to attain an excellent preservative effect.

To achieve the above aim, the present disclosure provides a paper substrate laminate for inhibiting ethylene response, comprising at least one layer of polymer composition and at least one layer of paper substrate, wherein the polymer composition comprises an agent that blocks binding sites for ethylene response in plants, a solvent having slight solvency or no solvency, and a polymer or copolymer soluble in the solvent and water. The composition can control the release of the agent that blocks binding sites for ethylene response in plants upon an action with water, thereby achieving a preservative storage and transportation of foods such as flowers, vegetables and fruits.

Preferably, in the laminate, the agent that blocks binding sites for ethylene response in plants as used is selected from a group consisting of cyclopropene, 1-methyl cyclopropene, methylene cyclopropene, 3,3-dimethyl cyclopropene, diazo cyclopentadiene, trans-cyclooctene, cis-cyclooctene, 2,5-norbornadiene, derivatives thereof and mixtures thereof.

Preferably, in the laminate, the agent that blocks binding sites for ethylene response in plants as used is 1-methylcyclopropene.

Preferably, in the laminate, the polymer or copolymer as used is a solid polymer of vinylpyrrolidone, which is selected from a group consisting of polymeric compounds of polyvinylpyrrolidone produced via a polymerization reaction of N-vinyl-2-pyrrolidone.

Preferably, in the laminate, the weight ratio of the polymer or copolymer to the agent that blocks binding sites for ethylene response in plants, as used, is between 30:1 and 1:1.

Preferably, in the laminate, the solvent having slight solvency or no solvency as used is selected from a group consisting of water, ethanol, chlorine, and an organic solvent other than ethyl ether, and the organic solvent other than ethyl ether is methanol, hexanol, dichloromethane, chloroform or benzene.

Preferably, the laminate further comprises a filler in tablet dosage or powder dosage, and the filler includes, but is not limited to, one or more of antibacterial agent, polymeric absorbent, chitosan, dextrin, clay and montmorillonite. The additional amount of the filler may be controlled within a suitable range as required.

Preferably, in the laminate, the agent that blocks binding sites for ethylene response in plants as used is released in the form of gas, namely, the agent is one that may be released in the form of gas upon an action with water.

The laminate is a multi-layered structure, preferably, the layer of the polymer composition that can release the agent that blocks binding sites for ethylene response in plants and the layer of the paper substrate are arranged alternately.

Preferably, the laminate further comprises a moisture-semipermeable membrane which is located on the outmost layer of the laminate.

Preferably, in the laminate, the moisture-semipermeable membrane as used is selected from a group consisting of urethane, polyamide, polyester, nylon and blends thereof.

Preferably, in the laminate, the paper substrate is an art paper or a matt art paper.

The present disclosure also provides a method for preparing a paper substrate laminate for inhibiting ethylene response in plants, comprising a step of laminating a layer of a polymer composition to a layer of paper substrate, wherein the polymer composition as used comprises an agent that blocks binding sites for ethylene response in plants and a polymer or copolymer.

According to an embodiment of the present disclosure, preferably, the method for preparing the paper substrate laminate for inhibiting ethylene response in plants may comprise the steps of:

mixing the agent that blocks binding sites for ethylene response in plants, a solvent having slight solvency or no solvency and the polymer or copolymer to obtain a liquid composition;

applying or spraying the liquid composition onto a surface of the substrate, wherein the liquid composition is applied in an amount of preferably 20 to 120 g/m2, more preferably 40 g/m2; and drying to obtain the paper substrate laminate for inhibiting ethylene response in plants.

Preferably, in the method, the solvent having slight solvency or no solvency as used is selected from a group consisting of water, ethanol, chlorine, and an organic solvent other than ethyl ether, and the organic solvent other than ethyl ether is methanol, hexanol, dichloromethane, chloroform or benzene.

Preferably, in the method, the solvent having slight solvency or no solvency is added in an amount of 50% or more based on the total mass of the liquid composition.

The present disclosure also provides a method for inhibiting ethylene response in plants, comprising using the paper substrate laminate for inhibiting ethylene response in plants.

The present disclosure also provides a method for preparing an aluminum foil laminate for inhibiting ethylene response in plants, comprising at least one layer of a polymer composition and at least one layer of aluminum foil, wherein the polymer composition as used comprises an agent that blocks binding sites for ethylene response in plants and a polymer or copolymer.

The present disclosure also provides a method for preparing a corrugated board laminate for inhibiting ethylene response in plants, comprising at least one layer of polymer composition and at least one layer of corrugated board, wherein the polymer composition as used comprises an agent that blocks binding sites for ethylene response in plants and a polymer or copolymer.

Based on a totally novel concept, the present disclosure is to dissolve 1-MCP encapsulated with cyclodextrin in a polymer soluble in the solvent and water and apply it onto a paper substrate, so as to address the problem of non-uniform distribution of 1-MCP powder in the non-woven fabric laminate, which not only allows 1-MCP to be uniformly transferred to a plant to inhibit ethylene response, but also allows the novel laminate according to the disclosure to be more convenient for use by a user, than the effervescent tablet and the non-woven fabric laminate. In addition, the hydroscopicity thereof can be adjusted by adjusting the type and ratio of the polymer composition, which provides a significant improvement that has not yet been achieved before the disclosure, for the preservation technique for a harvested plant.

The cyclodextrin is currently the best carrier for immobilizing the chemical gas that blocks binding sites for ethylene response in plants. Many application dosages currently known are produced by directly subjecting a powder composition having an agent that blocks binding sites for ethylene response in plants encapsulated with cyclodextrin, to subsequent processing, such as subpackaging the powder into pouches, compacting the powder into tablets, spraying the powder onto a substrate and so on.

In order to address the uniformity problem of directly processing powder, the present disclosure provides a polymer having not only an advantage of the stability of the agent that blocks binding sites for ethylene response in plants, encapsulated with cyclodextrin, but also an improvement of uniformity in the subsequent processing, so as to avert the restricts of the powder device and environment, while ensuring an effective release of the agent that blocks binding sites for ethylene response in plants, encapsulated with cyclodextrin when the product is used on-site.

Further areas of applicability will become apparent from the description provided herein. The description and specific examples in this summary are intended for purposes of illustration only and are not intended to limit the scope of the present disclosure.

DESCRIPTION

The technical solutions of the present disclosure will be described in detail below for a better understanding of the technical features, purpose and beneficial effect of the present disclosure, and should be construed as a limit of the scope implementable by the present disclosure.

The present disclosure provides a paper substrate laminate, comprising at least one layer of a polymer composition and at least one layer of paper substrate, wherein the polymer composition comprises an agent that blocks binding sites for ethylene response in plants, encapsulated with cyclodextrin, a solvent, in which cyclodextrin is slightly soluble or insoluble, and a polymer or copolymer soluble in the solvent and water.

According to the present disclosure, the term "plant" generally include, in addition to woody plants, the growing, harvested or picked field crops, potted plants, cut flowers, fruits, vegetables and ornamentals.

Plants treated by the paper substrate laminate of the present disclosure to inhibit the ethylene response need to be treated with a non-phytotoxic amount. This phytotoxic amount varies not only by the plant but also by the cultivar thereof.

According to the present disclosure, many ethylene responses may be prevented, as disclosed in U.S. Pat. Nos. 5,518,988 and 3,879,188. Ethylene responses may be initiated by either exogenous or endogenous sources of ethylene. Ethylene responses include, for example, ripening and/or senescence of flowers, fruits and vegetables; abscission of foliage, flowers and fruit; ripening and/or shortening of the life of ornamentals, such as potted plants, cut flowers, shrubbery and dormant seedlings; inhibition of growth in some plants such as pea; and stimulation of growth in some plants such as rice.

According to the present disclosure, the agent that blocking binding site for ethylene response in plants includes all the compounds conventionally used to inhibit ethylene response in plants, such as, but not limited to, cyclopropene, 1-methyl cyclopropene (1-MCP), 3-methyl cyclopropene, 3,3-dimethyl cyclopropene, methylene cyclopropene, diazo cyclopentadiene, trans-cyclooctene, cis-cyclooctene, 2,5-norbornadiene, derivatives thereof and mixtures thereof. The relevant prior arts, such as U.S. Pat. Nos. 3,879,188, 5,100,462 and 5,518,988, and Sisler et al., Plant Growth Reg. 9, 157-164, 1990 are incorporated herein by reference. Preferably, the agent that blocks biding sites for ethylene response in plants is 1-methylcyclopropene.

Numerous polymers or copolymers are suitable for use in the present disclosure, including, but not limited to, a solid vinylpyrrolidone polymer, including the most common polymeric compound, polyvinylpyrrolidone (abbreviated as PVP) which is produced via a polymerization reaction of N-vinyl-2-pyrrolidone. PVP is a highly hygroscopic, white powder with good water solubility, having no odor or slight odor, soluble in water, ethanol, chloroform and most organic solvents but insoluble in ethyl ether. PVP can be divided into four grades, and represented by K value, depending on the molecular weight thereof. The larger K value is, the larger the viscosity thereof is, and the stronger the adhesion is. PVP has been widely used in food clarifying agent, stabilizing agent, conditioning agent and dispersing agent and the like, due to its low toxicity and solubility in both water and most of organic solvents.

The hydroscopicity of the polymer composition in the present disclosure can be adjusted by adjusting the type and ratio thereof, and the polymer composition can be used for adjusting the release of the agent that blocks biding sites for ethylene response in plants upon an action with water.

The thermoplastic composition in the present disclosure can further comprises a filler in conventional tablet dosage or powder dosage, while the suitable filler includes, but not limited to, an antibacterial agent, dextrin, chitosan, polymeric absorbent, clay or montmorillonite.

The novel paper substrate laminate of the present disclosure has a major advantage in providing an ethylene-blocking agent that blocks binding sites for ethylene response in plants and having a good convenience and flexibility in use. The novel paper substrate laminate of the present disclosure can also reduce defects present in the process of mixing in the powder dosage product, and alleviate the problem of the tendency to distribute the powders of the ethylene-blocking agent non-uniformly in the non-woven fabric laminate. In use on-site, the paper substrate can be coated with an adhesive material, and is easy to be printed with a pattern and a QR codes for tracing the production and marketing history, while a tablet cannot individually have these functions. Non-woven fabric is a soft material and cannot be easily attached onto the package of vegetables, fruits and flowers, which is however an advantage of the present disclosure.

The method for bonding the polymeric laminate to a paper substrate has been well known for a period of time. However, there is no attempt in the prior art to apply such a concept in the technical field of preserving an agricultural product after its harvest. Generally speaking, any method can be used to produce the paper substrate laminate of the present disclosure, and the method is not specially limited as long as a laminate can be formed integrally.

The paper substrate laminate of the present disclosure may include an additional moisture-semipermeable membrane to adjust the moisture released from the agricultural product. In an example, when practically used, the moisture-semipermeable membrane is positioned at the outmost layer of the laminate facing the stored agricultural product. The typical moisture-semipermeable membrane may include, but not limited to, urethane, polyester, polyamide, nylon and blends of hydrophilic polymers of this kind.

The present disclosure also provides a method for using the paper substrate laminate of the present disclosure to inhibit ethylene response in plants. For example, the novel paper substrate laminate of the present disclosure can be cut into a suitable size for use as a cover sheet for vegetables, fruits or flowers stored in the container, or can be joined together via the edges of the paper substrate laminate or joined with a plastic bag to form a pouch shape, so as to store vegetables, fruits or flowers. In such a container or pouch, the moisture evaporated from a plant allows the ethylene-blocking agent to be released in the form of gas from the paper substrate laminate of the present disclosure.

According to the present disclosure, the paper substrate laminate can be extended to a multilayered structure comprising more than one layer of a polymer composition capable of releasing an agent that blocks binding sites for ethylene response in plants and more than one layer of paper substrate. The sequence and arrangement of layers in the multilayered structure can be determined according to the practical use.

In the other aspect of the present disclosure, the concept of paper substrate laminate can be applied to a laminate having a corrugated board, aluminum foil or other suitable substrate materials, or any other combinations thereof. The aluminum foil layer or corrugated board may be bonded to a layer of the polymer composition comprising a polymer or copolymer and an agent that blocks binding sites for ethylene response in plants via methods well-known to an ordinary person skilled in this art, including but not limited to, laminate of paper-aluminum foil-plastic film, laminate of wax-paper-aluminum foil-plastic film, and laminate of plastic film-paper-aluminum foil-plastic film, and the like.

Therefore, the present disclosure also provides a corrugated board laminate for inhibiting ethylene response in plants, comprising at least one layer of a polymer composition and at least one layer of corrugated board, wherein the polymer composition comprises an agent that blocks binding sites for ethylene response in plants and a polymer or copolymer.

The present disclosure also provides an aluminum foil laminate for inhibiting ethylene response in plants, comprising at least one layer of a polymer composition and at least one layer of aluminum foil, wherein the polymer composition comprises an agent that blocks binding sites for ethylene response in plants and a polymer or copolymer.

Without further elaboration, it is believed that an ordinary person skilled in the art can, based on the above disclosure and examples described below, utilize the present to its fullest extent. The following examples are to be construed as merely illustrative examples of how an ordinary person skilled in the art practice the methods of the present application and are not limitative of the remainder of the disclosure in any way.

EXAMPLES

Example 1: The Preparation Method

A blend of polyvinylpyrrolidone (PVP) and 1-methylcyclopropene powders having the following composition was laminated onto a paper substrate:
  2.75% of polyvinylpyrrolidone PVP VA64;
  8.24% of polyvinylpyrrolidone PVP K90;
  3.75% of 1-methylcyclopropene powders (AnsiP® from Lytone Enterprise, Inc. Taipei, Taiwan, PRC);
  61.54% of ethanol;
  23.72% of corn starch.

A liquid composition containing 1-MCP was prepared by weighing and mixing uniformly the above components in their ratios. The liquid composition was applied onto a surface of an art paper or a matt art paper substrate with a coating bar (RDS BAR COATER) in manual operation or mechanical drive, or the liquid composition was applied onto an art paper or a matt art paper substrate by using a spraying dispersion device throughout the working area of the art paper or matt art paper substrate. In this example, the material capable of releasing 1-MCP was laminated onto the paper substrate in an amount of 40 g/m$^2$. After being naturally dried, the coated paper was cut into a suitable size for analysis of the release of 1-MCP.

Example 2: Release of 1-MCP from the Paper Substrate Laminate

The 1-MCP release characteristic of the paper substrate laminate capable of releasing 1-MCP was measured through the following steps:

A laminate having an area of 5 cm×10 cm was placed in sealed sample vials under different environments to release 1-MCP. The released amount of 1-MCP was detected by GC at a regular time, and the released percentage of 1-MCP was calculated.

The method for preparing the sealed sample vials under different environments was as follows: the soaking condition was that the paper for detecting is directly and totally soaked in pure water at 25° C.; and the condition of 25° C., 89.9% RH was achieved by using a saturated barium chloride solution to achieve a condition of 89.9% RH in the sealed sample vials.

Table 1 shows the release of 1-MCP from the paper substrate laminate. It is clear from Table 1 that 1-MCP can be completely released under both storage conditions upon the application of water onto a surface of the paper substrate laminate capable of releasing 1-MCP.

TABLE 1

| Storage condition | Time (h) | Released percentage of 1-MCP (%) |
|---|---|---|
| Soaking | 1 | 62 |
|  | 3 | 80 |
|  | 5 | 100 |
|  | 7 | 100 |
|  | 24 | 100 |
| 25° C., 89.9% RH | 1 | 69 |
|  | 3 | 83 |
|  | 5 | 100 |
|  | 7 | 100 |
|  | 24 | 100 |

Example 3: Application

Totally green Taiwan tomatoes were tested to evaluate the performance of the paper substrate laminate capable of releasing 1-MCP according to the present disclosure. The paper substrate laminate capable of releasing 1-MCP was cut into a size of 5×10 cm. In the experiments, six Taiwan tomatoes were provided for treatment in an experimental group and a control group, respectively. In each of the treatments, the tomatoes were stored at room temperature in a sealed container having a volume of 4.675 L (90% to 95% RH) for 24 h, and then were removed for a mass observation.

The result shows that, at day 7 after storage at room temperature, the appearance of Taiwan tomatoes in the control group begins to turn red while the ones in preservative-paster treated group do not turn red at all; at day 11, the appearance of Taiwan tomatoes in the control group has turned red completely while the ones in the preservative-paster treated group just begins to turn red from green. From the above result, it can be known that the preservative paster can release 1-MCP in the fruit experiment and has an effect of delaying after-ripening of Taiwan tomatoes to an extent that the storage life of Taiwan tomatoes can be extended to about 14 days, while the ones in the control group, which do not use the present disclosure, only have a storage life of 7 to 11 days.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. In addition, advantages and improvements that may be achieved with one or more exemplary embodiments of the present disclosure are provided for purpose of illustration only and do not limit the scope of the present disclosure, as exemplary embodiments disclosed herein may provide all or none of the above mentioned advantages and improvements and still fall within the scope of the present disclosure.

Specific dimensions, specific materials, and/or specific shapes disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The term "about" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. For example, the terms "generally", "about", and "substantially" may be used herein to mean within manufacturing tolerances. Or for example, the term "about" as used herein when modifying a quantity of an ingredient or reactant of the disclosure or employed refers to variation in the numerical quantity that can happen through typical measuring and handling procedures used, for example, when making concentrates or solutions in the real world through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The foregoing description of the embodiments has been provided for purposes of illustration and description. It is not intended to be exhaustive or to limit the disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A paper substrate laminate for inhibiting ethylene response in plants, comprising at least one layer of a polymer composition and at least one layer of paper substrate, wherein the polymer composition comprises an agent that blocks binding sites for ethylene response in plants encapsulated with cyclodextrin, a solvent in which cyclodextrin is slightly soluble or insoluble, and a polymer or copolymer soluble in the solvent and water, wherein the paper substrate laminate is a multi-layered structure, wherein the layer of the polymer composition that release the agent that blocks binding sites for ethylene response in plants and the layer of the paper substrate are arranged alternately in the multi-layered structure, wherein the polymer or copolymer is a solid polymer of vinylpyrrolidone, which is selected from a group consisting of polymeric compounds of polyvinylpyrrolidone produced via a polymerization reaction of N-vinyl-2-pyrrolidone.

2. The laminate according to claim 1, wherein the agent that blocks binding sites for ethylene response in plants is selected from a group consisting of cyclopropene, 1-methylcyclopropene, methyl ene cyclopropene, 3,3-dimethyl cyclopropene, diazo cyclopentadiene, trans-cyclooctene, cis-cyclooctene, 2,5-norbornadiene, derivatives thereof and mixtures thereof.

3. The laminate according to claim 2, wherein the agent that blocks binding sites for ethylene response in plants is 1-methylcyclopropene.

4. The laminate according to claim 1, wherein a weight ratio of the polymer or copolymer to the agent that blocks binding sites for ethylene response in plants is between 30:1 and 1:1.

5. The laminate according to claim 1, wherein the solvent in which cyclodextrin is slightly soluble or insoluble is selected from a group consisting of water, ethanol, chlorine, and an organic solvent other than ethyl ether, and the organic solvent other than ethyl ether is methanol, hexanol, dichloromethane, chloroform or benzene.

6. The laminate according to claim 1, wherein the agent that blocks binding sites for ethylene response in plants is released in the form of gas.

7. The laminate according to claim 1, wherein the paper substrate is preferably an art paper or a matt art paper.

8. A method for preparing the paper substrate laminate for inhibiting ethylene response in plants according to claim 1, the method comprising a step of laminating the layer of the polymer composition to the layer of the paper substrate.

9. The method according to claim 8, wherein the method further comprises steps of:
mixing the agent that blocks binding sites for ethylene response in plants encapsulated with cyclodextrin, the solvent in which cyclodextrin is slightly soluble or insoluble and the polymer or copolymer to obtain a liquid composition;
applying or spraying the liquid composition onto a surface of the substrate; and
drying to obtain the paper substrate laminate for inhibiting ethylene response in plants.

10. The method according to claim 9, wherein the liquid composition is applied in an amount of 20 to 120 g/m2.

11. The method according to claim 10, wherein the liquid composition is applied in an amount of 40 g/m2.

12. The method according to claim 9, wherein the solvent in which cyclodextrin is slightly soluble or insoluble is selected from a group consisting of water, ethanol, chlorine, and an organic solvent other than ethyl ether, and the organic solvent other than ethyl ether is methanol, hexanol, dichloromethane, chloroform or benzene.

13. The method according to claim 9, wherein a mass of the solvent in which cyclodextrin is slightly soluble or insoluble is 50% or more relative to a total mass of the liquid composition.

14. A method for inhibiting ethylene response in plants, comprising using the paper substrate laminate for inhibiting ethylene response in plants according to claim 1.

15. A paper substrate laminate for inhibiting ethylene response in plants, comprising at least one layer of a polymer composition and at least one layer of paper substrate, wherein the polymer composition comprises an agent that blocks binding sites for ethylene response in plants encapsulated with cyclodextrin, a solvent in which cyclodextrin is slightly soluble or insoluble, and a polymer or copolymer soluble in the solvent and water, wherein the laminate further comprises a filler in tablet dosage and/or powder dosage, and the filler includes one or more of antibacterial agent, polymeric absorbent, chitosan, dextrin, clay and montmorillonite, wherein the polymer or copolymer is a solid polymer of vinylpyrrolidone, which is selected from a group consisting of polymeric compounds of polyvinylpyrrolidone produced via a polymerization reaction of N-vinyl-2-pyrrolidone, wherein the paper substrate is a multilayered structure, wherein the layer of the polymer composition that release the agent that blocks binding sites for ethylene response in plants and the layer of the paper substrate are arranged alternately in the multi-layered structure.

16. A paper substrate laminate for inhibiting ethylene response in plants, comprising at least one layer of a polymer composition and at least one layer of paper substrate, wherein the polymer composition comprises an agent that blocks binding sites for ethylene response in plants encapsulated with cyclodextrin, a solvent in which cyclodextrin is slightly soluble or insoluble, and a polymer or copolymer soluble in the solvent and water, further comprising a moisture-semipermeable membrane which is located on an outmost layer of the laminate, wherein the paper substrate laminate is a multi-layered structure, wherein the layer of the polymer composition that releases the agent that blocks binding sites for ethylene response in plants and the layer of the paper substrate are arranged alternately in the multi-layered structure, wherein the polymer or copolymer is a solid polymer of vinylpyrrolidone, which is selected from a group consisting of polymeric compounds of polyvinylpyrrolidone produced via a polymerization reaction of N-vinyl-2-pyrrolidone.

17. The laminate according to claim 16, wherein the moisture-semipermeable membrane is selected from a group consisting of urethane, polyamide, polyester, nylon and blends thereof.

* * * * *